United States Patent
Becerra et al.

(10) Patent No.: US 7,254,842 B2
(45) Date of Patent: Aug. 14, 2007

(54) SELF-EXAMINATION DEVICE

(75) Inventors: Carlos Becerra, Atlanta, GA (US); David Williams, Epping (GB)

(73) Assignee: Sante Feminine Limited, Marietta, GA (US)

( * ) Notice: Subject to any disclaimer, the term of this patent is extended or adjusted under 35 U.S.C. 154(b) by 71 days.

(21) Appl. No.: 10/978,851

(22) Filed: Nov. 1, 2004

(65) Prior Publication Data

US 2006/0090243 A1    May 4, 2006

(51) Int. Cl.
*A41D 19/00*    (2006.01)
(52) U.S. Cl. ..................................... 2/161.7
(58) Field of Classification Search ............... 2/16, 2/20, 21, 161.7, 161.8; 600/587; 601/134, 601/137, 138
See application file for complete search history.

(56) References Cited

U.S. PATENT DOCUMENTS

| | | | |
|---|---|---|---|
| 1,169,804 A | 2/1916 | Gregory | |
| 2,326,159 A | 8/1943 | Mendel | |
| 2,694,396 A | 11/1954 | Paschal | |
| 3,136,417 A | 6/1964 | Clinch | |
| 3,149,017 A | 9/1964 | Ehrreich et al. | |
| 3,633,216 A | 1/1972 | Schonholtz | |
| 4,143,423 A | 3/1979 | Sternlieb | |
| 4,657,021 A | 4/1987 | Perry et al. | |
| 4,793,354 A | 12/1988 | Wright et al. | |
| 4,919,966 A * | 4/1990 | Shlenker | 128/844 |
| 5,035,003 A * | 7/1991 | Rinehart | 2/159 |
| 34,353 A | 8/1993 | Perry et al. | |
| 5,946,727 A | 9/1999 | Wright et al. | |
| 2003/0109910 A1* | 6/2003 | Lachenbruch et al. | 607/108 |
| 2004/0107475 A1* | 6/2004 | Gogarty | 2/159 |

* cited by examiner

*Primary Examiner*—Katherine Moran
(74) *Attorney, Agent, or Firm*—Patton Boggs LLP

(57) ABSTRACT

A self-examination device including (i) a first layer formed of two sheets of material connected to form a plurality of enclosures encapsulating fluid therein and (ii) a second layer composed of a sheet of material opposing the first layer and attached to the first layer along a first portion to form a cavity between the first and second layers. The second layer is unattached to the first layer along a second portion to form an opening to the cavity to receive at least a portion of a hand to enable a person to perform a self-examination via the enclosures of the first layer.

31 Claims, 4 Drawing Sheets

SELF-EXAMINATION DEVICE

BACKGROUND OF THE INVENTION

1. Technical Field of the Invention

The principles of the present invention are generally directed to a self-examination device, and more particularly, but not by way of limitation, to a self-examination device that includes multiple enclosures having lubricating fluid at the finger locations to enhance effectiveness for detecting abnormalities in the human anatomy.

2. Description of Related Art

Breast cancer is one of the leading causes of death in women. Early detection of the cancer is one of the most important ways for treating the disease. Typically, breast cancer is detected when lumps formed in the breast are detected. The lumps can be detected by X-ray radio photography (mammography). However, women generally receive mammograms once a year after the age of forty. While the frequency of once a year for having a mammogram is beneficial, breast cancer not detected by a mammogram may develop rapidly between mammograms. A fast developing cancer may advance to a stage that requires more advanced treatment within the one-year period between mammograms.

Because having a mammogram at a frequency of one-year may not be often enough for some breast cancers, women are encouraged to perform self-examinations of their breasts to feel for lumps. Self-examinations of the breasts may result in a higher rate of early detection of lumps or other abnormality that is or may lead to breast cancer.

There are a number of techniques for a self-examination of the breast to be performed, including standing and lying while wet and dry. Generally, a self-examination in the bath and shower with water and soap is recommended, but creams may be used outside of the bath or shower. However, while these techniques are recommended, women often fail to perform the self-examinations or fail to perform the self-examination correctly for a variety of reasons. In the case where women simply fail to perform the breast self-examination, the leading reasons include embarrassment, lack of skill, forgetfulness, religious beliefs, etc. In the case of women not performing the breast self-examination correctly, the leading reasons include poor technique, dry skin, positioning, lack of sensitivity, etc.

To assist women in remembering to perform breast self-examinations and assisting to perform better quality and more thorough breast self-examinations, self-examination devices have been developed. These self-examination devices include pads and mittens.

A self-examination pad is typically configured as two sheets of material having a circular shape and sealed about the perimeter to form an enclosure having a lubricant contained or encapsulated therein. The size of the pad is typically six inches or more (i.e., about the size of a hand) in diameter. The sheets of materials are typically formed of soft, pliable, elastic, and smooth material. Elastomers, either natural or synthetic, are suitable for use as the sheets of material that have been deemed to satisfy the requirements for a self-examination device as understood in the art. The lubricant has traditionally been soapy water, silicon, or any other fluid that is capable of operating as a lubricant to enable the two sheets forming the pad to slide in relation to one another when being pressed together during the self-examination. As understood in the art, the pad is used by being pressed between the breast or other part of the human anatomy (e.g., testicle) and fingers. The sheet that is pressed against the skin remains fixed in place in relation to the skin while the sheet being pressed by the fingers remains fixed in relation to the fingers, but slides in relation to the other sheet, thereby making it easier for a person to feel for lumps in the breast, for example, rather than artifacts on the skin.

A self-examination mitten is generally constructed in a similar manner as the self-examination pad with the exception of having an added sheet of material connected to a pad to form a pocket or cavity so as to enable a person to insert a hand into the mitt to engage the hand. However, in both the case of the pad and mitt, the fluid contained in the enclosure tends to flow to the bottom of the enclosure (i.e., near a person's wrist) due to gravity, thereby making the self-examination devices more difficult to use because the lubricant flows to areas of the enclosure that are not being rubbed together during the self-examination.

SUMMARY OF THE INVENTION

To overcome the problem of fluid in self-examination devices from draining from areas of the self-examination device that are being pressed during the self-examination process, the principles of the present invention provide for a self-examination device including (i) a first layer formed of two sheets of material connected to form a plurality of enclosures encapsulating fluid therein and (ii) a second layer composed of a sheet of material opposing the first layer and attached to the first layer along a first portion to form a cavity between the first and second layers. The second layer is unattached to the first layer along a second portion to form an opening to the cavity to receive at least a portion of a hand to enable a person to perform a self-examination via the first layer.

In using the self-examination device on a part of the human anatomy according to the principles of the present invention, a person may insert at least a portion of a hand into an examination device including two layers. A first layer includes at least two sheets of material to form a plurality of enclosures encapsulating fluid therein. A second layer is attached to the first layer and an opening is defined between the first and second layers. An examination is performed on a part of the human anatomy by pressing at least one finger against the part of the human anatomy via at least one enclosure.

BRIEF DESCRIPTION OF THE DRAWINGS

The disclosed invention will be described with reference to the accompanying drawings, which show sample embodiments of the invention and which are incorporated in the specification hereof by reference, wherein.

DETAILED DESCRIPTION OF THE EXEMPLARY EMBODIMENTS

Figure 1A:
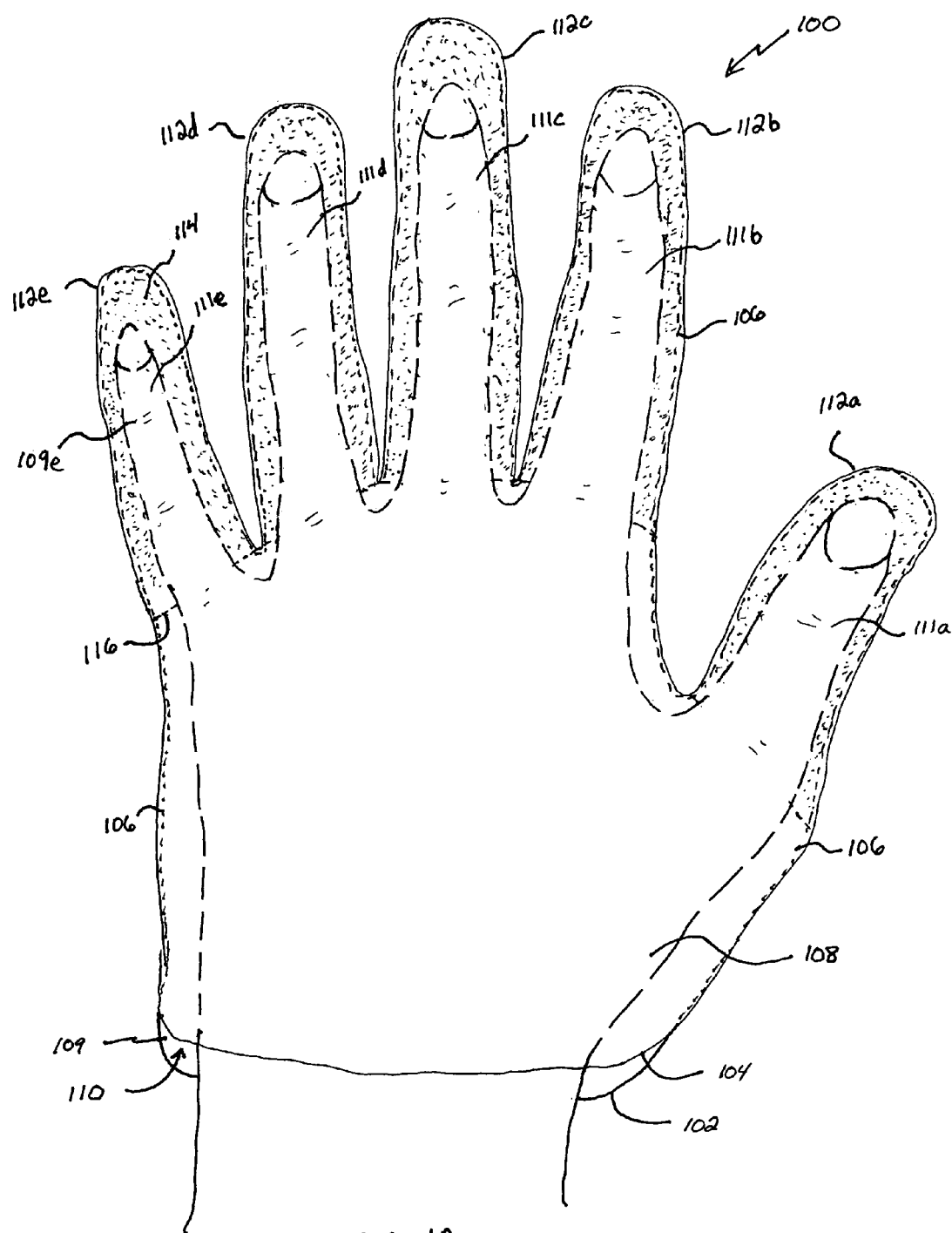
FIG. 1A illustrates a top view (back of hand) of an exemplary self-examination device having a plurality of enclosures containing fluid for providing lubrication between a first and second sheet of material according to the principles of the present invention.

FIG. 1A illustrates a top view (back of hand) of an exemplary self-examination device 100. The self-examination device 100 includes a first layer 102 and a second layer 104. The first and second layers 102 and 104 are connected via a seal 106, shown as a dashed line about the perimeter of the first and second layers 102 and 104. The seal 106 may be formed by a melting process, stitching process, or other process capable of securing the first and second layers as understood in the art. The first and second layers 102 and 104 may have an unattached portion 109 along the perimeter of the first and second layers 102 and 104. The edges of the first and second layers 102 and 104 at the unattached portion 109 maybe unaligned when the layers are substantially contiguous to facilitate separation of the layers. Alternatively, an opening in the material of one of the first or second layers 102 and 104 may enable the hand 108 to be inserted into a cavity 110 so that the first and second layers 102 and 104 engage the hand 108. In an alternative embodiment, the second layer 104 may simply form a strap when connected to the first layer 102. As shown, the first layer is located on the palm side of the hand 108 and the second layer is located on the back side of the hand 108 when the hand 108 is inserted into the cavity 110 formed between the first and second layers 102 and 104.

The first and second layers 102 and 104 may be shaped in the form of a hand such that the self-examination device 100 functions as a glove. Fingers 111a-111e (collectively 111) may be inserted into individual finger cavities 112a-112e (collectively 112) formed between the first and second layers 102 and 104. The finger cavities 112 are formed by the seal 106 of the first and second layers 102 and 104.

The first layer 102 may be formed by two sheets of material that have a fluid 114 enclosed therebetween in enclosures. The sheets of material may be composed of elastomers or other soft, smooth, and flexible material as understood in the art. The fluid 114 provides lubrication between the first and second sheets of the first layer 102 and may be a soap and water mixture, silicone, or any other lubricating fluid that enables the sheets of material to slide in relation to one another when pressed together. As shown, another seal 116 is formed at the bottom of each of the finger cavities 112 of the first layer 102 so that enclosures extending along each of the finger cavities 112 in the first layer 102 maintains the fluid 114 generally where a person presses while performing a self-examination.

Figure 1B:
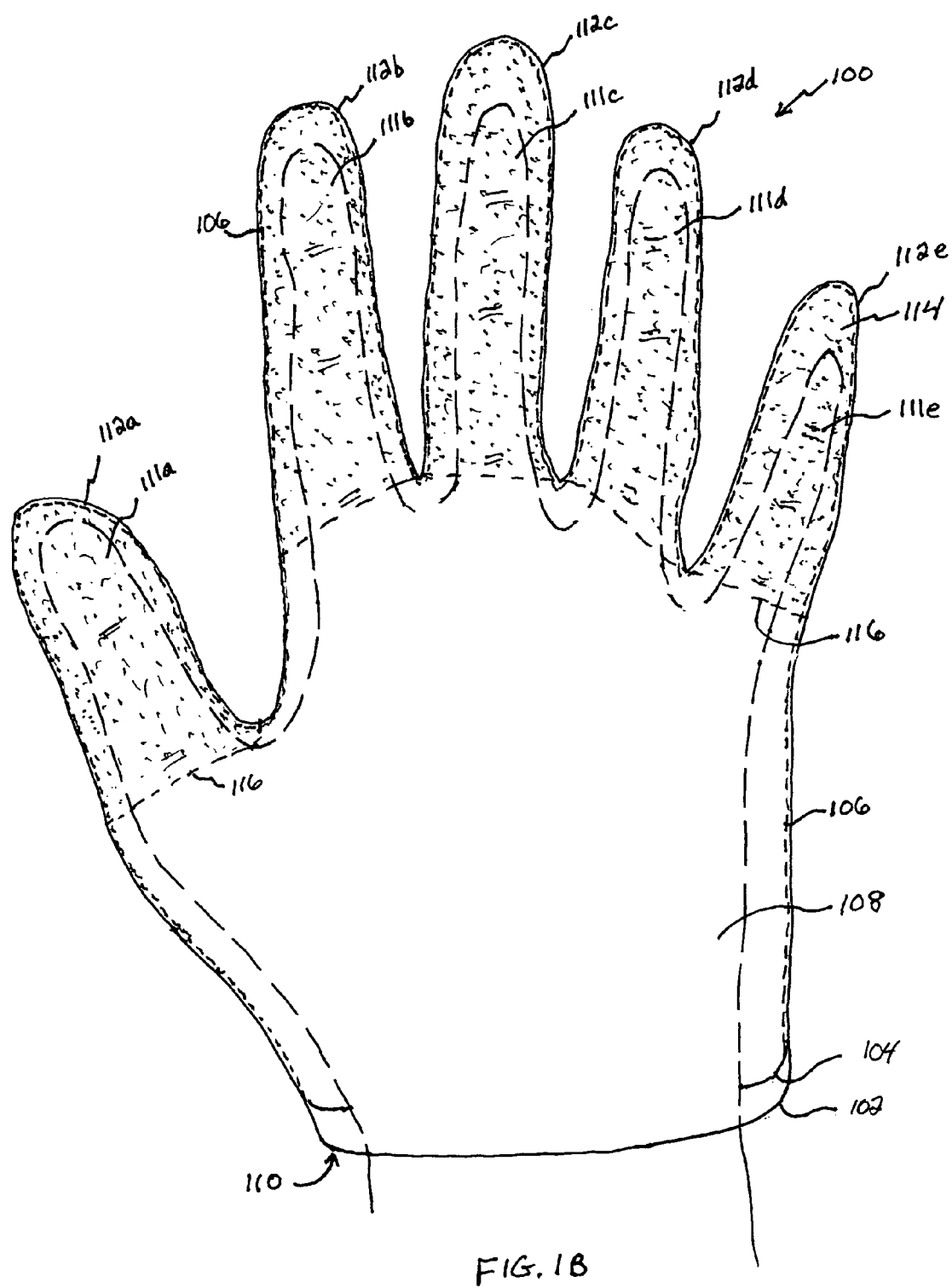
FIG. 1B illustrates a bottom view (palm view) of the exemplary self-examination device of FIG. 1A.

FIG. 1B illustrates a bottom view (palm view) of the exemplary self-examination device 100 of FIG. 1A. As shown, the hand 108 is inserted into the cavity 110 between the first and second layers 102 and 104 and the fingers 111 extend into the finger cavities 112. The fluid 114 is maintained within the first layer 102 (i.e., between two sheets of material) within the multiple enclosures at the fingers by the seal 116 instead of seeping down to the palm or wrist due to gravitational effects. The seal 116 may be formed as a single, continuous seal or multiple, distinct seals. It should be understood that the seal 116 may be higher or lower than the bottom of each of the fingers as depicted in FIG. 1B, but the result of including a seal at or above the finger cavities 112 is to maintain the fluid 114 at or near the fingertips where a person has the most sensitivity while performing a self-examination of her or his anatomy (e.g., breast, testicle).

Figure 2A:
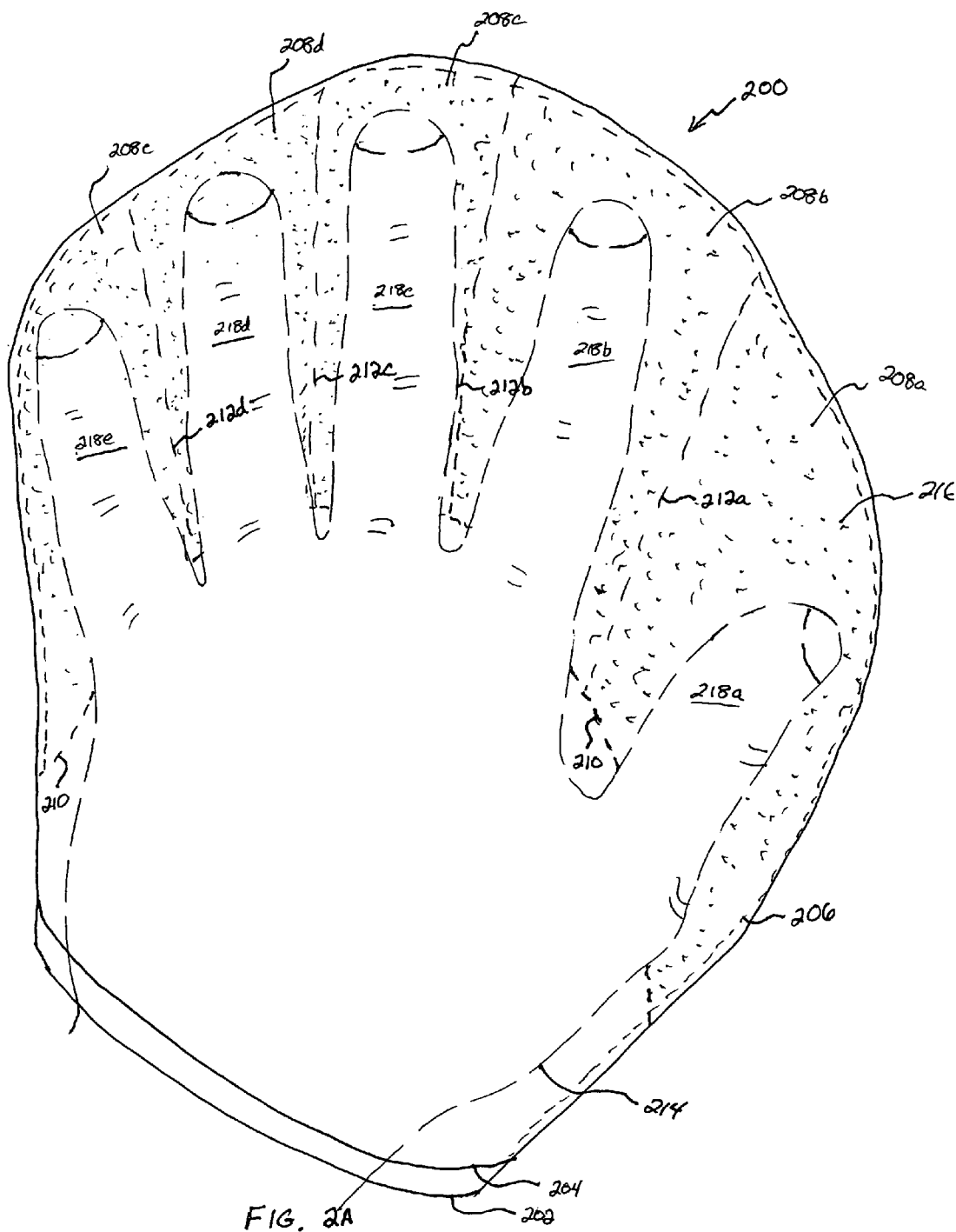
FIG. 2A illustrates another exemplary self-examination device configured as a mitt having a plurality of enclosures containing fluid along each finger region.

FIG. 2A illustrates another exemplary self-examination device 20 configured as a mitt. As shown, there are first and second layers 202 and 204 that form the palm side and back hand side, respectively, of the self-examination device 200. The first and second layers 202 and 204 are connected via a seal or other connection mechanism at or above the perimeter of the first and second layers 202 and 204. As shown, the first and second layers 202 and 204 are shaped as a mitt. It should be understood that other shapes may be utilized in accordance with the principles of the present invention.

The first layer 202 may be formed of two sheets of material having multiple enclosures 208a-208e (collectively 208) defined by seals 210 and 212a-212d (collectively 212). The seal 210 at or about the bottom of each enclosure 208 maintains fluid 216 at the fingers 218a-218e (collectively 218). The seals 212 may extend from the seal 210 to the seal 206 located at the perimeter of the first layer. It should be understood that the seal 210 may be located closer to or farther from the tips of the fingers 218.

Figure 2B:
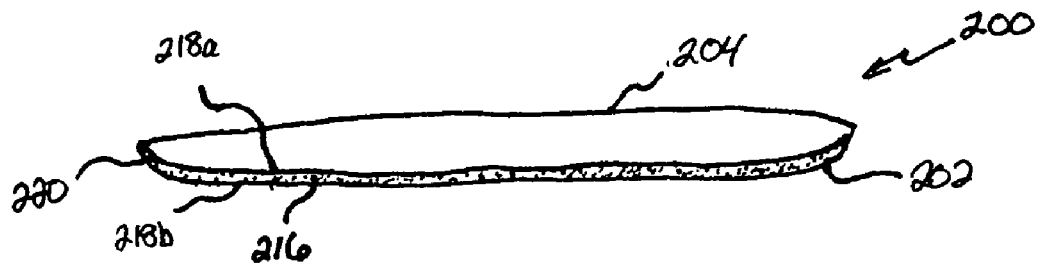
FIG. 2B is an end view of a self-examination device showing a first layer having fluid contained therein and a second layer.

FIG. 2B is an end view of the self-examination device 200 of FIG. 2A including the first layer 202 and second layer 204 connected thereto. The first layer 202 may be formed of the fluid 216 encapsulated by two sheets of material 218a and 218b (collectively218) that form an enclosure 220. The enclosure 220 may be separated into multiple enclosures for each finger or a group of fingers of a person's hand to engage. By forming multiple enclosures, the fluid 216 may be maintained at locations that are most used while performing a self-examination such that the effects of gravity on the fluid do not substantially reduce the effectiveness of the self-examination device. It should be understood that a single enclosure that is positioned substantially at the fingers or finger tips may be utilized, but that the relative effectiveness of the self-examination device relative to the multiple enclosure design may be decreased due to the fluid having more area to flow due to gravitational effects. Of course, additional fluid may be included in the enclosure to compensate for the larger area. In another embodiment, two enclosures may be formed, one for the fingers and one for the thumb.

Figure 3:
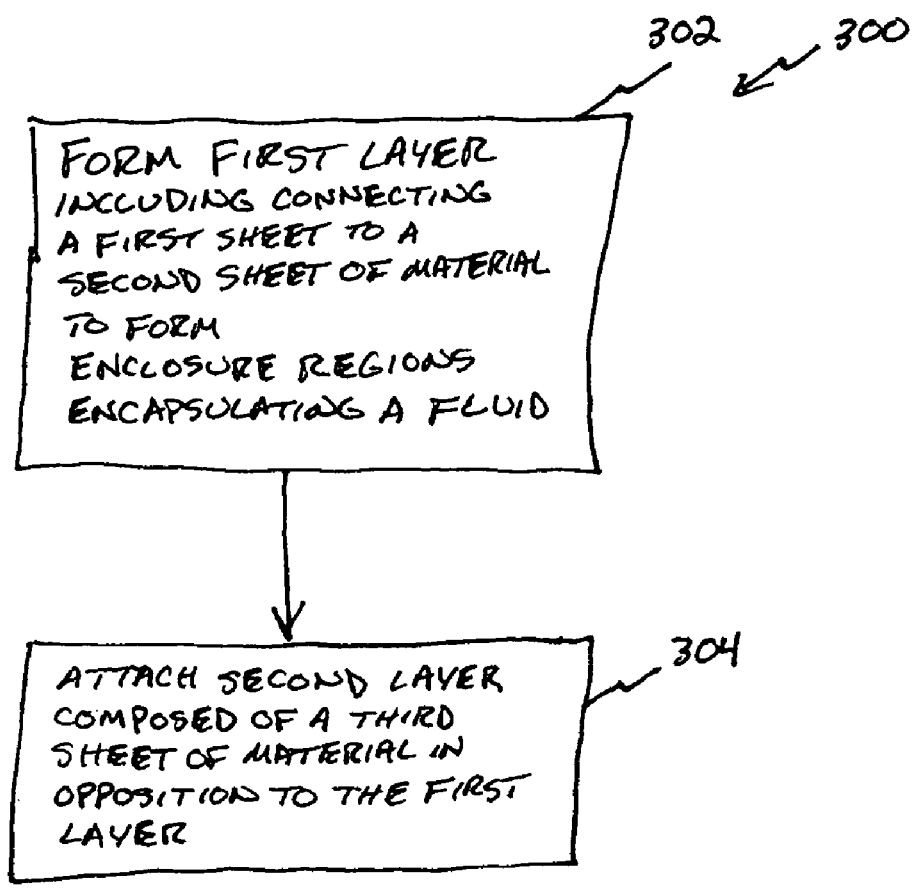
FIG. 3 shows an exemplary flow chart describing the manufacturing of a self-examination device according to the principles of the present invention.

FIG. 3 shows an exemplary flow chart describing the manufacturing of a self-examination device 300 according to the principles of the present invention. The manufacturing process starts at step 302 where a first layer is formed including connecting a first sheet of material to a second sheet of material to form enclosures encapsulating a fluid. The sheets of material may be formed of elastomers or other soft, pliable, elastic, smooth material. The fluid may be any lubricant that enables the first sheet to slide in relation to the second sheet while being used to perform a self-examination. At step 304, a second layer composed of a third sheet of material is attached to the first layer in opposition thereto so as to form a cavity or other opening in which at least the portion of a hand may be inserted for performing the self-examination. In one embodiment, a cavity is created between the first and second layers. The cavity may include additional cavities extending from a primary cavity for fingers to be inserted. The fluid enables the fingers to press into an inner sheet of the first layer to slide in relation to outer sheets of the first layer while being used during a self-examination.

The innovative concepts described in the present application can be modified and varied over a wide range of applications. Accordingly, the scope of patented subject matter should not be limited to any of the specific exemplary teachings discussed, but is instead defined by the following claims.

We claim:

1. A self-examination device, comprising:
   a first layer forming at least one enclosure encapsulating fluid therein; and
   a second layer opposing the first layer and attached to the first layer along a first portion of the second layer to form a cavity between the first and second layers and unattached to the first layer along a second portion of the second layer to form an opening to the cavity to receive at least a portion of a hand to enable a person to perform a self-examination by applying pressure to the enclosures of the first layer, the first and second layers together defining a palm region and at least one finger region, the at least one enclosure encapsulating fluid being located substantially within the finger region and no enclosures encapsulating fluid within the palm region.

2. The device according to claim 1, wherein the first and second layers are attached along the perimeters.

3. The device according to claim 1, wherein the first layer has a profile in the shape of a hand.

4. The device according to claim 1, wherein the cavity is in the shape of a hand.

5. The device according to claim 1, wherein the fluid is a lubricant.

6. The device according to claim 5, wherein the fluid is silicone.

7. The device according to claim 1, wherein the first layer is formed at least in part of two sheets of material, the sheets of material are composed of elastomers.

8. The device according to claim 1, wherein the unattached second portion is along the perimeter of the second layer.

9. The device according to claim 1, wherein the enclosures are located at an opposite end of the first layer from the opening to the cavity to enable the person to engage fingers of the band with the enclosures.

10. The device according to claim 1, wherein the self-examination is a breast examination.

11. The device according to claim 1, wherein the self-examination is a testicle examination.

12. The device according to claim 1, wherein the device is in the shape of a mitten and includes separate cavities for fingers.

13. The device according to claim 1, wherein the at least one enclosure includes five enclosures.

14. The device according to claim 1, wherein the plurality of enclosures include two enclosures.

15. The self-examination device of claim 1, wherein the first layer is composed of two sheets of material connected to form the at least one enclosure encapsulating the fluid.

16. A method of manufacturing a self-examination device, comprising:
    forming a first layer formed of a at least one enclosure encapsulating fluid therein;
    attaching a second layer in opposition to the first layer along a first portion of the second layer to form a cavity between the first and second layers, a second portion of the second layer being unattached to the first layer to form an opening to the cavity to receive at least a portion of a hand to enable a person to perform a self-examination by applying pressure to the enclosures of the first layer, and the first and second layers together defining a palm region and at least one finger region; and
    positioning the at least one enclosure encapsulating fluid substantially within the finger region and no enclosure encapsulating fluid within the palm region.

17. The method according to claim 16, wherein the attaching is performed along the perimeter of the first and second layers.

18. The method according to claim 16, further comprising shaping the first layer in the profile of a hand.

19. The method according to claim 16, wherein the attaching of the first and second layers results in a cavity in the shape of a hand.

20. The method according to claim 16, wherein the forming includes sealing the fluid in the at least one enclosure.

21. The method according to claim 20, wherein the forming includes sealing a fluid composed of silicone in the at least one enclosure.

22. The method according to claim 16, wherein the attaching includes connecting the first and second layers about the perimeter of the first layer in all but a portion of the perimeter of the second layer.

23. The method according to claim 16, wherein the attaching of the second layer to the first layer positions the at least one enclosure at an opposite end of the first layer from the opening to the cavity to enable the person to engage fingers of the hand with the at least one enclosure.

24. The method according to claim 16, wherein the attaching the first and second regions forms a cavity in the shape of a mitten.

25. The method according to claim 16, wherein the forming the first layer includes forming five enclosures.

26. The method according to claim 16, wherein the forming the first layer includes forming two enclosures.

27. A method for performing an examination on a part of the human anatomy, said method comprising:
    inserting at least a portion of a hand into an examination device including two layers, a first layer forming at least one enclosure encapsulating fluid therein and a second layer being attached to the first layer and defining an opening between the first and second layers, the first and second layers together defining a palm region and a finger region, the at least one enclosure encapsulating fluid being located substantially within the finger region and no enclosures encapsulating fluid located in the palm region; and
    performing an examination of a part of the human anatomy by pressing at least one finger against the part of the human anatomy via at least one enclosure of the first layer.

28. The method according to claim 27, wherein the inserting includes inserting at least two fingers between the first and second layers and within the finger region, whereby at least two of the fingers engage different enclosures.

29. A self-examination device, comprising:
    a first layer forming at least one enclosure encapsulating fluid therein, said first layer including two sheets of material connected to form the at least one enclosure; and
    a second layer attached to the first layer to form a cavity between the first and second layers and to form an opening to the cavity for receiving a portion of a hand, the first and second layers each having an edge at the opening, the edges of the layers being unaligned when the layers are substantially contiguous, a seal connecting the two sheets and located substantially between the finger and palm regions, whereby the unaligned edges facilitate separation of the layers upon receiving the portion of a hand into the opening to the cavity to perform a self-examination by applying pressure to the at least one enclosure of the first layer.

30. The self-examination device according to claim 29, wherein the unalignment between the edges of the first and second layers provides for the edge of the second layer to be exactly positioned at the opening and the edge of the first layer to be positioned away from the opening.

31. The self-examination device according to claim 29, wherein the two sheets of material of the first layer are connected to form two or more enclosures encapsulating fluid therein.

* * * * *